United States Patent [19]
Ginsberg

[11] Patent Number: 5,527,275
[45] Date of Patent: * Jun. 18, 1996

[54] AUTOMATED EAR CLEANSING DEVICE

[76] Inventor: Irwin A. Ginsberg, 897 Delaware Ave., Buffalo, N.Y. 14209

[*] Notice: The term of this patent shall not extend beyond the expiration date of Pat. No. 5,309,899.

[21] Appl. No.: 238,301

[22] Filed: May 5, 1994

Related U.S. Application Data

[63] Continuation-in-part of Ser. No. 984,368, Dec. 2, 1992, Pat. No. 5,309,899, which is a continuation-in-part of Ser. No. 815,524, Jan. 9, 1992, Pat. No. 5,170,779, which is a continuation-in-part of Ser. No. 643,484, Jan. 21, 1991, abandoned.

[51] Int. Cl.$^6$ .............................. A61H 9/00; A61M 5/178; A61M 37/00
[52] U.S. Cl. ............... 604/38; 604/131; 604/150; 601/155
[58] Field of Search ................... 604/27, 30, 38, 604/131, 150; 433/80, 84; 601/155

[56] References Cited

U.S. PATENT DOCUMENTS

5,309,899   5/1994   Ginsberg .................................. 604/131

Primary Examiner—Randall L. Green
Assistant Examiner—Dennis Ruhl
Attorney, Agent, or Firm—Howard J. Greenwald

[57] ABSTRACT

A system for cleansing a patient's ear is disclosed. This system contains a control unit, a portable applicator, and a means for modifying the flow of fluid from the device when temperature or pressure limits are exceeded. The control unit contains a heater and control means for maintaining the temperature of the liquid within certain limits, for limiting the pressure of the liquid, and for varying the flow rate of the liquid. The portable applicator contains a handpiece, a nozzle which is connected to the fluid source and is mounted on the handpiece, and a means for providing a signal to the control unit.

15 Claims, 11 Drawing Sheets

AUTOMATED EAR CLEANSING DEVICE

CROSS-REFERENCE TO RELATED PATIENT APPLICATIONS

This case is a continuation-in-part of applicant's copending patent application 07/984,368, which was filed on Dec. 2, 1992 and will issue as U. S. Pat. No. 5,309,899 on May 10, 1994, which in turn was a continuation-in-part of United States patent application 07/815,524, which was filed on Jan. 9, 1992 and issued as U. S. Pat. No. 5,170,779 on Dec. 15, 1992, which in turn was a continuation in part of application 07/643,484, filed on Jan. 21, 1991, now abandoned.

FIELD OF THE INVENTION

An automated system for cleaning a patient's ear which contains a control unit, a portable applicator connected to the control unit, and means adapted to cause fluid flow through the portable applicator to cease when temperature limits are exceeded.

BACKGROUND OF THE INVENTION

Devices for the irrigation of a person's ear or the removal of wax from an ear are well known to those skilled in the art. Thus, for example, such devices are disclosed in U. S. Pat. No. 4,411,265 of Eichenlaub, 4,206,756 of Grossan, and 4,201,212 of Bradley.

None of the prior art ear irrigation devices are entirely satisfactory; none of them provide an automated ear flushing system which will readily and effectively control the flow rate, the pressure, and the temperature of the fluid delivered to the patient's ear.

It is an object of this invention to provide an automated ear flushing apparatus that will effectively control the flow, pressure, and temperature of fluid delivered to a patient's ear.

It is another object of this invention to provide an automated ear flushing apparatus that will control the pulsation of the fluid flow delivered to the patient's ear.

It is yet another object of this invention to provide an automated ear flushing apparatus with a handpiece which is lightweight, balanced in the operator's hand, and easily and comfortably manipulated during the cleaning operation.

It is another object of this invention to provide an automated ear flushing apparatus that can readily and easily be used by relatively unskilled operators.

It is another object of this invention to provide an automated ear flushing device comprised of an in-line heater.

It is another object of this invention to provide an automated ear flushing device containing an external reservoir;

It is yet another object of this invention to provide an automated, self-contained ear flushing device which may be held in a user's hand.

SUMMARY OF THE INVENTION

In accordance with this invention, there is provided a system for cleansing a patient's ear which contains a control unit, a portable applicator, and a means for modifying the flow of fluid from the device when temperature or pressure limits are exceeded.

The control unit contains a heater, a pump, and control means for maintaining the temperature of the liquid within certain limits, for limiting the pressure of the liquid, and for varying the flow rate of the liquid.

The portable applicator contains a handpiece, a nozzle which is connected to the fluid source and is mounted on the handpiece, and a means for providing a signal to the control unit.

BRIEF DESCRIPTION OF THE DRAWINGS

The present invention will be more fully understood by reference to the following detailed description thereof, when read in conjunction with the attached drawings, wherein like reference numerals refer to like elements, and wherein.

DESCRIPTION OF THE PREFERRED EMBODIMENTS

Figures 1, 2, 3, 4:
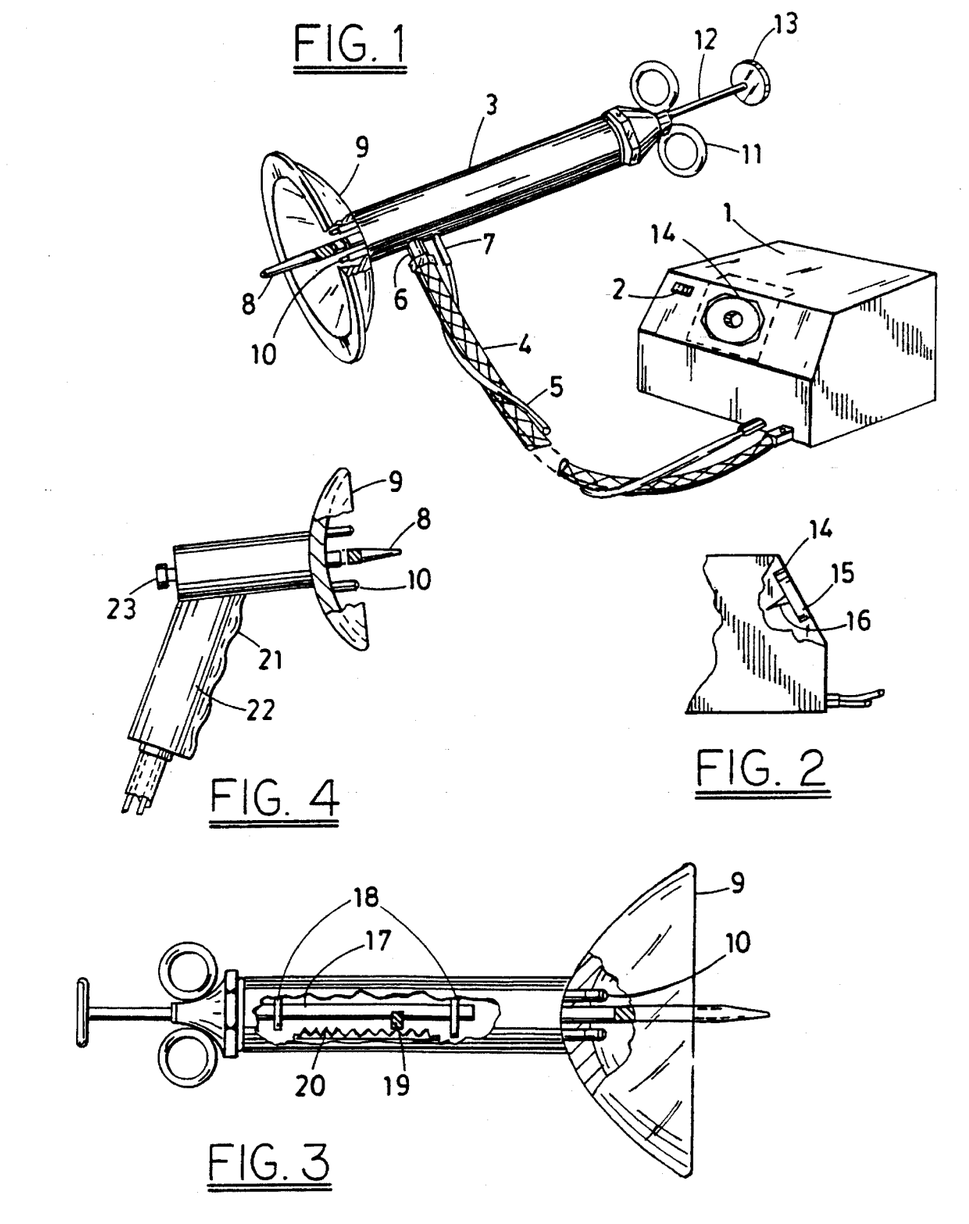
FIG. 1 is a perspective view of one preferred embodiment of the apparatus of this invention.
FIG. 2 is a partial side view of the controller of the apparatus of FIG. 1.
FIG. 3 is a partial side view of the handpiece applicator of the apparatus of FIG. 1.
FIG. 4 is a side view of another embodiment of a handpiece applicator which may be used in the apparatus of FIG. 1.
Figure 7:
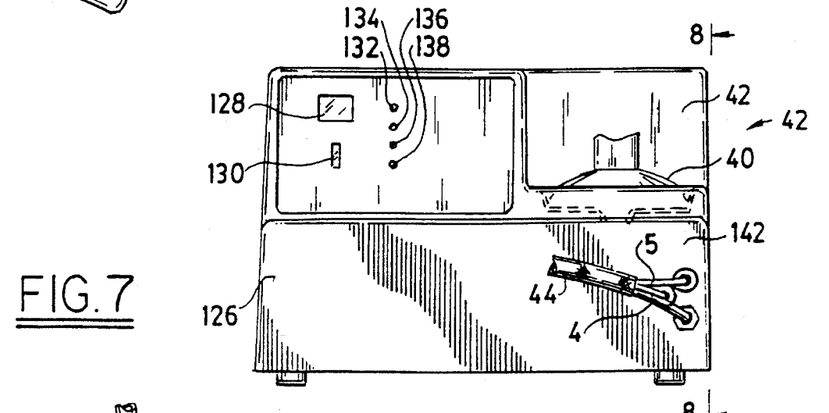
FIG. 7 is a front view of one embodiment of a controller which may be used with the applicator of FIG. 6.
Figure 8:
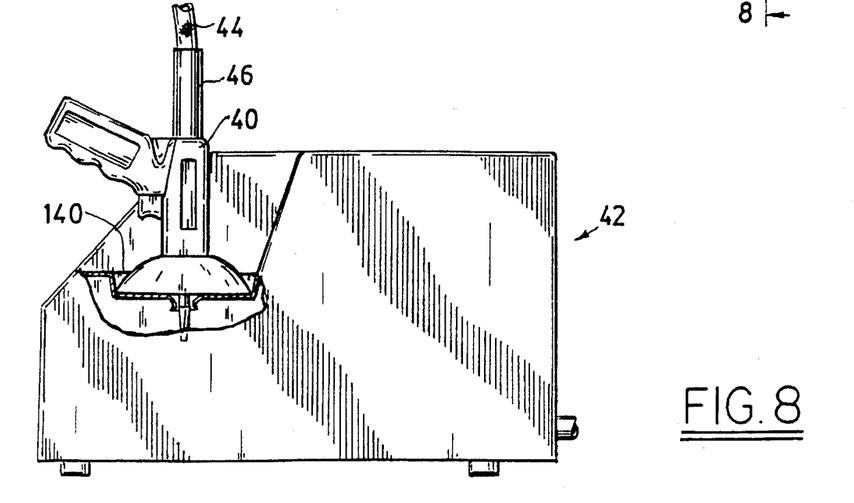
FIG. 8 is a side view of the controller of FIG. 7.

FIG. 1 is a representational perspective of one embodiment of applicant's device. Referring to FIG. 1, it will be seen that controller 1 is shown in the background of FIG. 1 with switching/status indicator device 2 preferably disposed in a compact front opening of such controller. Another embodiment of the controller 1 is illustrated in FIGS. 7 and 8 and will be discussed elsewhere in this specification.

Figure 5:
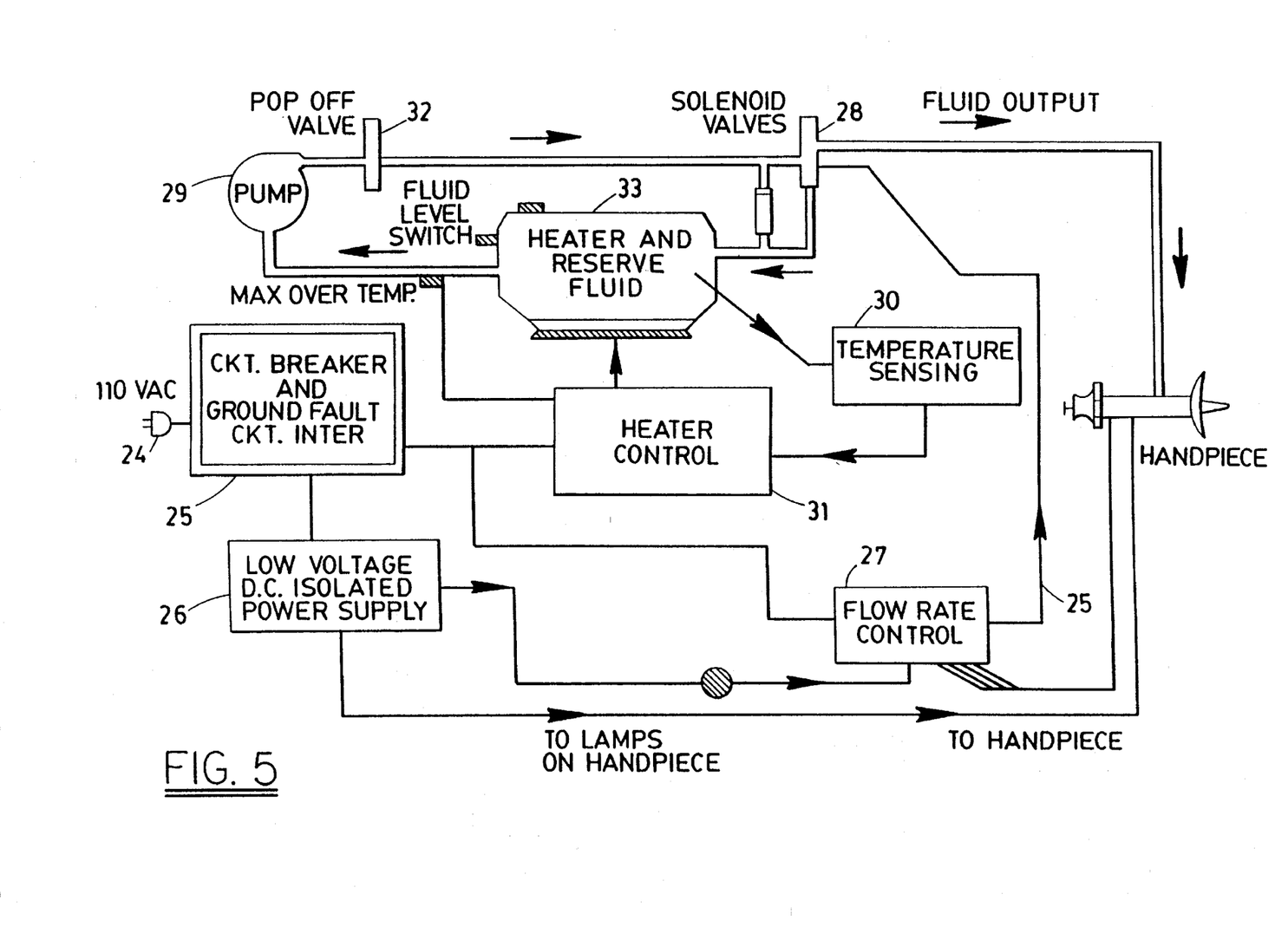
FIG. 5 is a block diagram illustrating the operation and functions of the controller of the apparatus of FIG. 1.

The controller 1 preferably contains a fluid reservoir (not shown in FIG. 1, but see FIG. 5). In one embodiment, the fluid reservoir is not used but is replaced with an in-line heater.

The controller 2 also preferably contains controlled thermostatic heating means (not shown in FIG. 1, but see FIG. 5) for precise temperature control of fluid, and pumping components (not shown in FIG. 1) for delivery of fluid through the system at selected pressures and pulsation flow patterns. The reservoir can be refilled manually as it is emptied.

Referring again to FIG. 1, it will be seen that the handpiece unit 3, which simulates a standard syringe configuration, is operatively connected to controller 1 by tubing 4 (which provides a water flow pathway) and wire sheath 5 (which contains a pair of controller signal leads). The wire sheath 5 may also include an illumination line, either to provide current to an otoscope-type incandescent bulb illumination means in the handset, or to provide direct illumination by light transmission through a fiber optic cable. The water tubing 4 is connected to the handpiece 3 by a water line fitting 6, and it is connected to the electrical line by electric jack 7. If fiber optic illumination is incorporated, the jack would also contain fittings to connect the fiber optic cable from the control unit to the optic terminus within the handpiece.

At the application end of the handpiece unit is nozzle 8; a jet applicator nozzle is illustrated in the Figures, but the nozzle style can be modified to provide a different flow pattern.

Surrounding the nozzle area, and separating it from the body of the handpiece and from the operator, is a concave-convex disk transparent shield 9, which can be constructed of appropriate glass or plastic material. Shield 9 serves to contain the flow and reduce back splash while enabling unobstructed view of the application of flow to the patient's ear. The transparent shield 9 further serves to facilitate viewing the operating area by magnifying the transmitted light or image by virtue of appropriate shaping of the curvature of the disk as a magnifying lens. Viewing is further enabled by lighting means within the convex portion of the shield, here shown as lenses 10, which transmit focused light from behind the lenses 10 provided either by electric bulbs or the terminus of fiber optic cables transmitting light from the control unit 1.

In this embodiment, the handpiece unit 3 is intentionally configured to simulate a standard valving syringe and is configured with finger rings 11 and thumb rest 13 at the extreme end of the plunger shaft 12. The function of the plunger shaft to operate an internally-contained slide potentiometer 20 to send an appropriate control signal to the controller 1. As the plunger 12 responds to the pressure of the user's thumb and is pushed into the handpiece unit, the resistance of the slide potentiometer 20 is proportionally varied and, in turn, signals the control unit 1 to increase or decrease the flow rate.

Maintenance of a constant temperature of the fluid applied to the patient's ear canal is often extremely important. Because operation of the unit may be intermittent, provision is made for maintaining the temperature in all parts of the system at a constant level by providing a storage receptacle 14 (see FIG. 2) for placement of the handpiece 3 in a resting position on the control unit 1.

FIG. 2 illustrates in cutaway view a portion of the controller 1 showing the configuration of the handpiece storage receptacle 14. Referring to FIG. 2, it will be seen that receptacle 14 includes an indentation 15 configured to contain the splash guard of the handpiece and an indentation 16 configured to contain the nozzle of the handpiece when it is placed in resting position in the control unit. A sensing switch is contained within the receptacle, and when the handpiece is placed therein will commence a low flow rate circulation from the reservoir through the tubing 4 and the handpiece nozzle 8, which in turn is directed back to the reservoir. Without this continuous recycling to maintain constant temperature, the temperature of residual water in the handpiece 3 and tubing 4 would decrease quickly to ambient temperature, and commencement of the flushing operation would subject the patient to a temperature variation as the fluid was exhausted from the tubing 4 and replaced by warmer reservoir water. The recirculating procedure in the resting state avoids this problem completely and maintains the fluid to close tolerance of body temperature. An appropriate output can also be easily included to control an indicator on the face of the control unit 1 showing actual temperature. Alternatively, a simple green light may be used for indicating temperature within operating limits.

FIG. 3 is a sectional side view of the handpiece 3 illustrating operation of the control signal. Referring to FIG. 3, it will be seen that plunger shaft extension 17 is disposed within the interior of handpiece 3, rests on a pair of guide supports 18, and is attached to contact 19.

Contact 19 is preferably located at about the midpoint of the potentiometric resistance 20. Movement of the plunger 12 varies the resistance and, consequently, the signal fed to controller 1. It is preferred that the controller 1 be programmed to provide a maximum flow rate when the plunger 1 is in the forward most position on the slide potentiometer 20 in relation to the nozzle end of the unit and conversely is in a shutoff condition when the plunger is withdrawn to the other end of the slide potentiometer 20.

Referring again to FIG. 2, and to the base of splash guard 9, the configuration of the light sources placed within the concave side of the shield 9 as lenses 10 will be seen. Lenses 10 are preferably directed to illuminate the working area.

FIG. 4 shows an alternative, pistol style handpiece 21 which is attached to an ergonomically designed hand grip 22 and is operated by a plunger thumb piece 23. The plunger thumb piece operates potentiometer 20 in the same manner as plunger 12. It will be apparent to those skilled in the art that a variety of other handpiece styles are possible which can incorporate the principles of applicant's invention. In particular, any electrical actuating device that can provide a signal proportional to the displacement of actuator could be incorporated into the handpiece. Thus, by way of illustration, one may use a piezoelectric device, a stepped series of discrete contacts or solid state devices, or an optical or laser-powered position indicator. Thus, e.g., instead of the syringe and pistol configurations described hereinabove, a bulb-style syringe or an illuminating otoscope configuration could easily be adapted to practice of the within invention and offer familiarity of instrumentation to many different individual operators.

FIG. 5 is a block diagram which illustrates a number of functions and advantages of the system consisting of the controller 1 and its operatively connected handpiece applicator 3. The operations and connections shown are representational, with fluid pathways in double lines and electrical power and signal pathways in single lines.

The unit depicted in FIG. 5 is intended for ordinary operation in an office environment, and it is configured to be powered by a standard 110 volt alternating current power connector 24 through a safety circuit breaker 25 in the form of a modern ground fault low-voltage isolated direct current power supply 26 contained within the housing of the controller unit 1. Circulating water pump 29 and heater control 31 are also contained within the housing within the housing of the controller 1.

The output of the low-voltage direct current power supply 26 is directed primarily to the flow-rate control 27 which is appropriately programmed to vary the flow rate signal to the solenoid valves 28 that control the flow output of pump 29 to application nozzle 8 at handpiece 3. Thus, the flow-rate control 27 receives the output signal of the potentiometer 20 from the handpiece 3 and generates an appropriate command to the solenoid valves 28 which will selectively open in metered fashion to provide a precisely indicated and controlled pressure and flow rate and further can operate in rhythmic fashion to provide a pulsing flow to the handpiece.

The fluid reservoir 33 is schematically represented and contains a heater element and fluid level switch and an appropriate temperature sensor which will generate a proportional electrical signal to the temperature sensing unit 30 which is in turn operatively connected to heater control 31 and will both operate the heater when the temperature drops out of limits and indicate a shutoff signal to the valves if the fluid temperature is outside operating range, preventing flow to the patient until the fluid is the proper temperature. An pressure relief valve 32 is additionally provided at the downstream of the pump for safety, and additional safety is provided by setting the flow controller 27 to operate the valve 28 if pressure exceeds a preset value.

In the preferred embodiment the illustrated, the flow rate control 27 is programmed and configured to control the pulsing rate and intensity of fluid injection, varying from slow and low pressure, increasing in linear fashion into faster pulsing rate and higher pressure, and finally to a continuous stream. Thus, the maximum control and variability is placed in the practitioner's hands. It is the wide range of selectability of the flow and pressure characteristics of the water stream that, in the hands of a skilled operator, can most efficiently perform the cleansing process, even to the dislodgement of especially stubborn obstructions of ear wax, while maximizing patient comfort and virtually eliminating mishandled applications that have in the past caused many patients pain.

DESCRIPTION OF ANOTHER PREFERRED EMBODIMENT OF THE INVENTION

Another preferred embodiment of applicant's system is illustrated in FIGS. 6 through 13. The handpiece 40 of this system is illustrated in FIGS. 6, 8, 10, 11, 12, and 13. The controller 42 of this system is illustrated in FIGS. 7 and 8. A block diagram illustrating the operations and functions of controller 42 is presented in FIG. 9.

The embodiment of the invention illustrated in FIGS. 6–13 differs from the embodiment illustrated in FIGS. 1–5 in several respects. In the first place, the latter system transmits light to the handpiece 40 by fiber optic means, thereby providing a cooler light source whose use is less likely to irritate a patient. In the second place, the latter system allows an operator to vary the flow of fluid delivered from the device with the same hand used to hold the device, thereby facilitating the use of the system. In the third place, controller 42 provides some additional and/or different functions and indicators which are not provided by controller 1.

Figure 6:
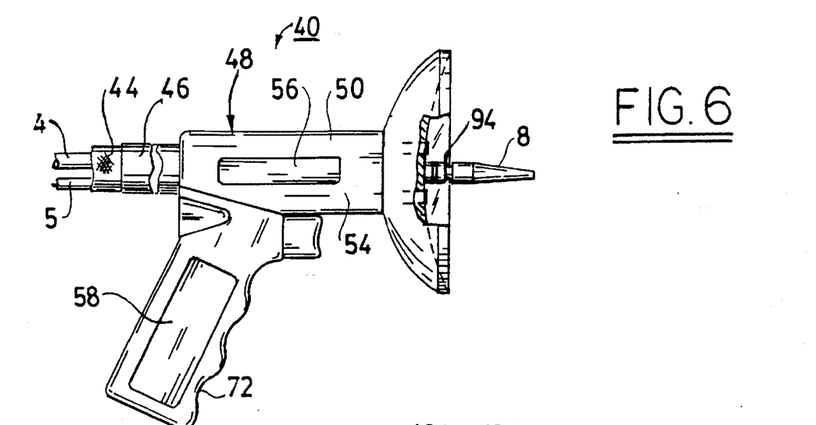
FIG. 6 is a side view of yet another embodiment of a handpiece applicator which may be used in the apparatus of this invention.

Referring to FIG. 6, it will be seen that handpiece 40 is connected to controller 42 by means of fluid line 4 (which provides a water flow pathway) and line 5. In the embodiment illustrated, line 5 encloses both an electrical line (for transmitting electrical information from handpiece 40 to controller 42) and a fiber optic line (for transmitting light from controller 42 to handpiece 40). In another embodiment, not illustrated, a separate line passing from the controller 42 to the handpiece 40 is used to transmit water, electrical signals and/or power, and light to and/or from the handpiece 40. Thus, e.g., in this embodiment an electrical signal is transmitted from the handpiece 40 to the control device 42.

In yet another embodiment, not shown, the signal transmitted from the handpiece to the controller is not an electrical signal but may be, e.g., an pneumatic signal. Those skilled in the art are aware of means for producing a nonelectrical signal by actuating a control device.

The water line 4 is preferably constructed of a plastic material which will not dissolve in water to any appreciable extent under the conditions of use. Thus, by way of illustration, one may use polyvinyl chloride tubing for the water line. Other suitable plastic materials will be apparent to those skilled in the art.

A nylon sheath 44 is used to enclose lines 4 and 5. Other conventional means of enclosing the fiber optic line and/or the water line and/or the electrical line(s) may also be used.

In the preferred embodiment illustrated in FIGS. 6 and 8, the sheathed lines are surrounded by a strain relief enclosure 46 which may be integrally joined to the body 48 of handpiece 40 or, alternatively, may be removably connected to body 48. Strain relief enclosure 46 preferably consists essentially of plastic material; however, other materials and/or other configurations may also be used as a strain relief means for lines 4 and 5.

The body 48 of handpiece 40 is preferably made from a plastic material, such as acrylonitrile-butadiene-styrene ("ABS") plastic. As will be apparent to those skilled in the art, other suitable materials also may be used.

Figure 10:
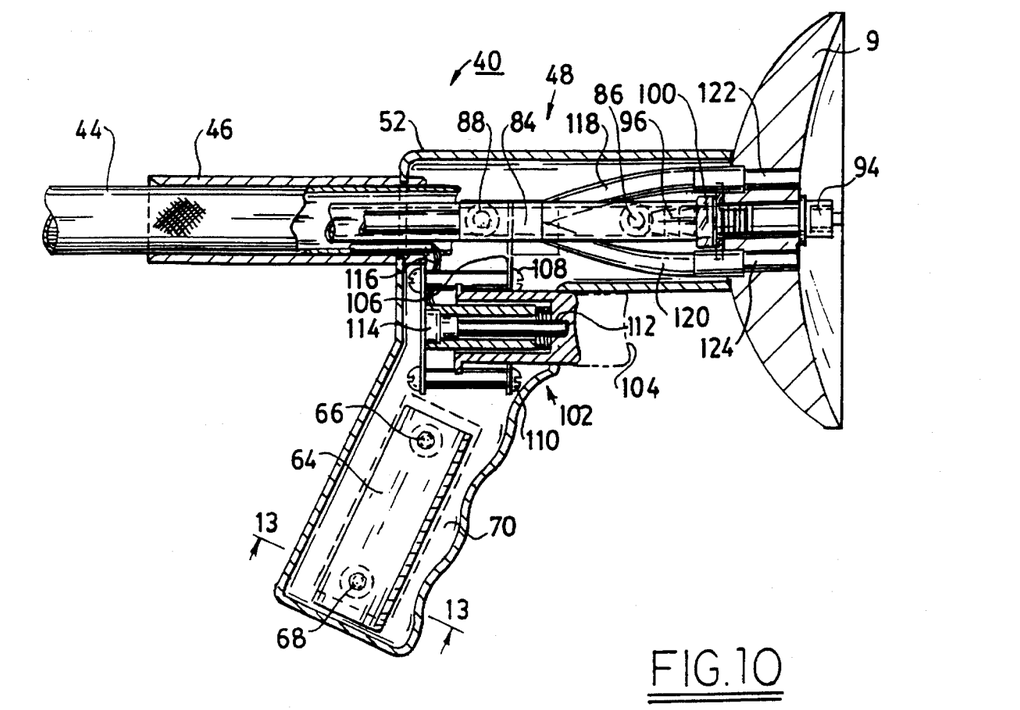
FIG. 10 is a side sectional view of the handpiece applicator of FIG. 6.
Figure 11:
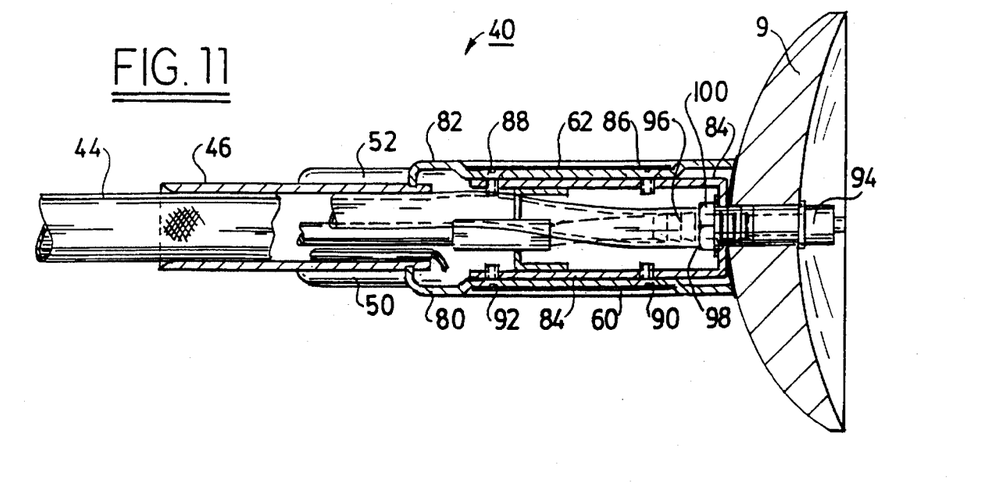
FIG. 11 is a top sectional view of the handpiece applicator of FIG. 6.
Figure 12:
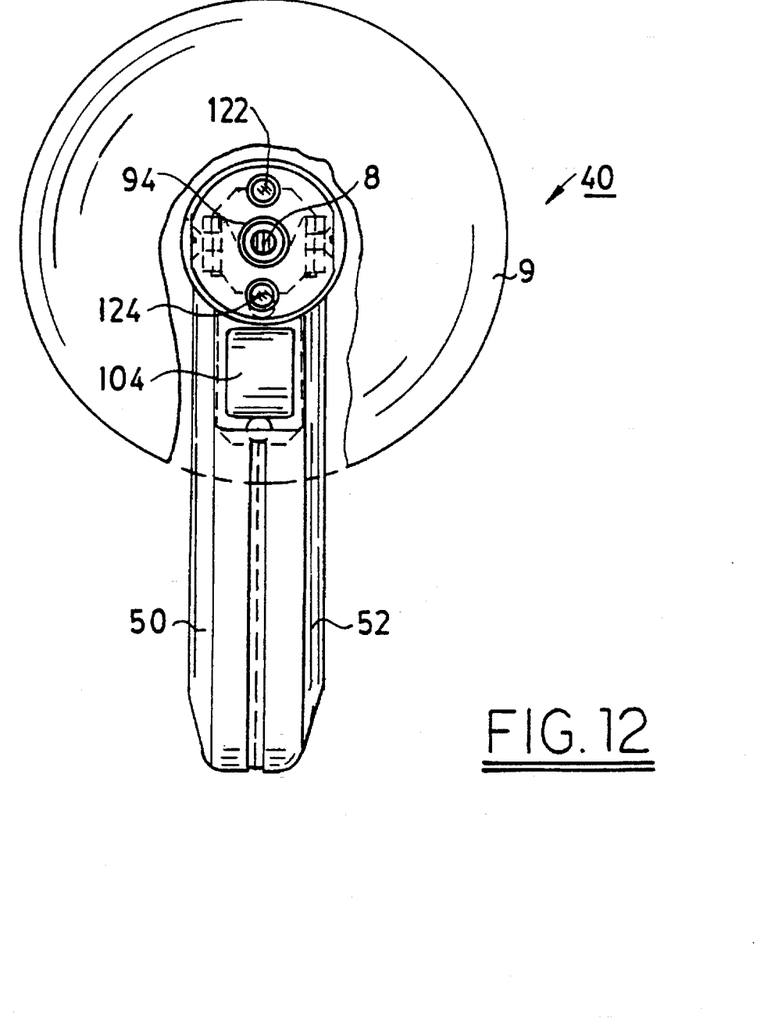
FIG. 12 is a front view of the handpiece applicator of FIG. 6.

In the embodiment illustrated in FIGS. 6, 11, and 12, body 48 is preferably comprised of two plastic parts which are secured together by suitable fastening means. One of such parts, right body side 50, is illustrated in FIGS. 6 and 11. Another of such parts, left body side 52, is illustrated in FIGS. 10 and 11.

Referring to FIG. 6, it will be seen that the exterior surface 54 of right body part 50 preferably defines two recessed areas (not shown) which are covered with decorative material 56 and decorative material 58; these recessed areas are comprised of orifices (not shown) for the passage of fasteners therethrough. Decorative materials 56 and/or 58 may be of a different color than body part 50. Alternatively, or additionally, such decorative material may contain letters and/or numbers indicating the name of the device (such as the "earigator") and/or its manufacturer.

Although not shown in FIG. 6, it will be appreciated that similar recessed areas are also present in left body part 52. FIG. 11 illustrates that each of body parts 50 and 52 is comprised of recessed areas 60 and 62 respectively. FIG. 10 illustrates that body part 52 is also comprised of recessed area 64. Although not shown in the Figures, it will be appreciated by those skilled in the art that a recessed area comparable to that of recessed area 64 is also present in body part 52.

Each of the recessed areas is preferably comprised of at least two orifices through which fasteners may be inserted. Thus, referring to FIG. 10, orifices 66 and are provided in recessed area 64; and screws (not shown in FIG. 10) may be inserted through orifices 66 and 68 to help secure the handle portion 70 of body part 52 to the corresponding handle portion 72 (not shown in FIG. 10, but see FIG. 6) of body part 50.

Figure 13:
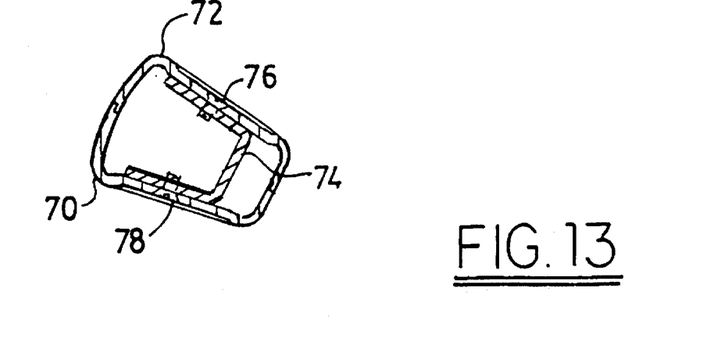
FIG. 13 is a front sectional view of the handle of the handpiece applicator of FIG. 6.

FIG. 13 is a front sectional view of the handle of handpiece applicator 40. Referring to FIG. 13 it will be seen that, in the embodiment illustrated therein, a bracket 74 is disposed between handle part 70 and handle part 72; this bracket 74 contains threaded orifices. Screws 76 and 78 are passed through orifices in handle portions 72 and 70, respectively, to secure handle portions 72 and 70 to bracket 74.

Referring again to FIG. 11, it will be seen that, in addition to handle portions 72 and 70, respectively, each of body parts 50 and 52 is also comprised of a barrel portion 80 and 82, respectively. In the embodiment illustrated in FIGS. 6–11, barrel portion 80 is integrally connected to handle portion 72, and barrel portion 82 is integrally connected to handle portion 70.

Referring again to FIG. 11, and in the embodiment illustrated therein, it will be seen that barrel portions 80 and 82 are preferably each connected to a substantially U-shaped bracket 84 by means of screws 86, 88, 90, and 92.

Referring again to FIG. 6, it will be seen that nozzle 8 is preferably removably connected to Luer lock 94. In one embodiment, nozzle 94 preferably consists essentially of plastic material and may be disposed of after one use.

Any means for removably attaching nozzle 8 to applicator 40 may be used in applicant's device. Thus, referring to FIGS. 10 and 11, one may use any of the conventional Luer to bulkhead adaptors for this purpose. Thus, by way of illustration and not limitation, one may use Luer to bulkhead adaptor A1440 described in catalog M-91 of the S4J Manufacturing Services, of 374 Remsen Avenue, New Brunswick, N.J. 08901. Other means for removably attaching nozzle 94 to applicator 40 also may be used.

Referring again to FIGS. 10 and 11, an adaptor 96 is connected to Luer lock 94; adaptor 96 is adapted to receive the end 98 of water line 4 and to transmit water from water line 4 to nozzle 8. The adaptor 96 is secured to bracket 84 by means of nut 100.

Referring to FIG. 10, it will be seen that the trigger assembly 102 is connected to a descending bracket 106 which, in turn, is connected to U-shaped bracket 84; an opening (not shown) is provided in bracket 106 so that trigger 104 may extend through it. Screws 108 and 110 help secure trigger assembly 102 to bracket 106.

One preferred means for delivering am amount of water from nozzle 8 when trigger 104 is depressed is illustrated in FIG. 10. Referring to FIG. 10, it will be seen that trigger assembly 102 is comprised of a chamber 112 within which a pin (not shown) is disposed. One end of the pin is connected to trigger 104 and, thus, is moved when said trigger 104 is moved. The other end of said pin contains a reflective end.

In this preferred embodiment, trigger assembly 102 is also comprised of reflective assembly 114 which shines a beam of light on the reflective end of the pin and measures the reflectance from said reflective end. Any suitable reflective assembly known to those skilled in the art may be used as reflective assembly 114. Thus, by way of illustration, one may use Reflective Assembly HOA1397, which is available from the Honeywell Optoelectronics Company of 830 East Arapaho Road, Richardson, Tex. 75081.

As the pin is moved in chamber 112, the reflectance measured by reflective assembly 114 varies, and the signal generated by the reflective assembly 114 also varies. This varying signal is then transmitted through wires 116 in line 5 to controller 42.

Figure 9:
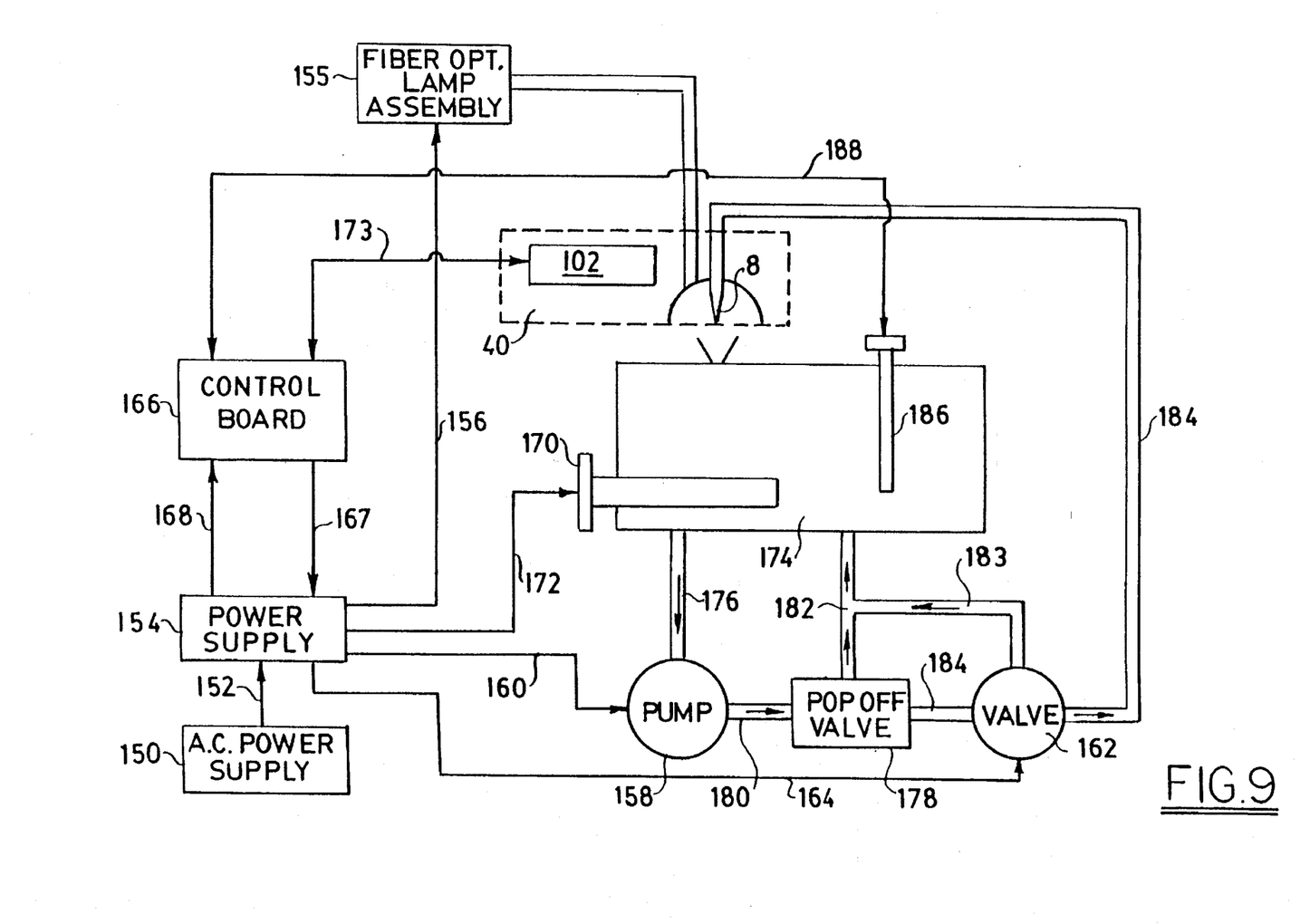
FIG. 9 is a block diagram of the operations and functions of the controller of FIGS. 7 and 8.

Controller 42 is programmed so that, when it receives a certain signal from trigger assembly 102, it transmits a signal to solenoid valve 162 which causes a pulsed water output to be delivered via line 184. When the signal received from trigger assembly 102 is increased a certain amount, the pulse rate of the pulsed water output delivered via line 184 also is increased. However, when the signal received from trigger assembly 102 is increased even further, a continuous stream of water is caused to be delivered via line 184.

Depending upon the extent to which, if any, the water delivered to line 184 is to be pulsed by the solenoid, a portion of the water delivered to solenoid valve from pop off valve 178 is returned to reservoir 174 via lines 183 and 182. Thus, for example, when trigger 104 is depressed to its maximum extent, and thus indicates to the control board 166 that a continuous stream of water is to be delivered via line 184, none of the water delivered to the solenoid valve 182 is vented via line 183.

Referring again to FIG. 10, it will be seen that fiber optic lines deliver light through openings 122 and 124, respectively, of convex disk transparent shield 9. In one preferred embodiment, convex disk transparent shield 9 is made out of acrylic material.

Referring again to FIG. 6, in the operation of applicant's system light will be delivered by fiber optic means through openings in shield 9. As trigger 104 is depressed, controller 42 will deliver a suitable amount of pulsed and/or continuous water through line 4 and nozzle 8, provided that the water is within the correct temperature and pressure ranges, as determined by controller 42.

FIG. 7 is a front view of one preferred embodiment of controller 42, illustrating the various indicia on said controller. Referring to FIG. 7, it will be seen that the front face 126 of controller 42 is preferably comprised of a water temperature gauge 128 indicating the temperature of the water in the controller reservoir, in degrees centigrade a "full/refill" gauge 130 indicating the extent to which the reservoir is filled with water, an on-off light emitting diode ("LED") 132 indicating "ready," an on-off LED 134 indicating "handpiece active," an on-off LED 136 indicating "water over temperature," and an on-off LED 138 indicating "place handpiece in cradle."

FIG. 8 is a side view of controller 42, showing handpiece 40 disposed in storage receptacle 140. Storage receptacle 140 operates in a manner similar to that of storage receptacle 14. However, because controller 42 has a different configuration than controller 1, storage receptacle 140 is located in a different area. Referring to FIGS. 7 and 8, it will be seen that controller 42 is comprised of a recessed area extending backwardly from its right front side 142.

FIG. 9 is a block diagram illustrating the operations and functions of controller 42. Referring to FIG. 9, it will be seen that alternating current power inlet 150 furnishes alternating current via line 152 to power supply 154. Power supply 152 supplies direct current, at the required voltage and amperage, to fiber optic lamp assembly 155 (via line 156), pump 158 (via line 160), solenoid valve 162 (via line 164), and control board 166 (via line 168). In addition, power supply 154 supplies alternating current to heater 170 (via line 172).

In the operation of the system, a signal is generated when trigger 104 of trigger assembly 102 is depressed. This signal is transmitted to control board 166 via line 173. In turn, control board 166 sends a signal to power supply 154, which in turn furnishes power to pump 158 via line 160.

Pump 158 draws water from reservoir 174 via line 176 and thence pumps the water to pop off valve 178 via line 180.

When the water pressure in line 180 exceeds a specified safe limit, pop off valve 178 diverts a portion of the water from pump 158 back to reservoir 174, via line 182; a sufficient amount of said water is thus vented to reduce the water pressure to a safe level.

Water at the proper pressure is passed via line 184 to solenoid valve 162 and thence, via line 184, to nozzle 8.

Sensor 186, which is disposed within reservoir 174, senses both the fluid level and the water temperature within the reservoir. This information is transmitted via line 188 to control board 166, which transmits this information via line 167 to power supply 154. This information also may be displayed with one or more of the indicia on the face of controller 42.

When the sensor 186 senses that the water temperature in reservoir 174 is outside of specifications, it will transmit this information to control board 166 which, in turn, will cause the power being transmitted to pump 158 to cease to flow. Additionally, it will also cause the power being supplied to heater 170 to cease to flow.

In one embodiment, not shown, heater temperature 170 also contains an over temperature switch which will cause the heater to cease operating when the temperature is too high.

The receptacle of this invention

Figure 14:
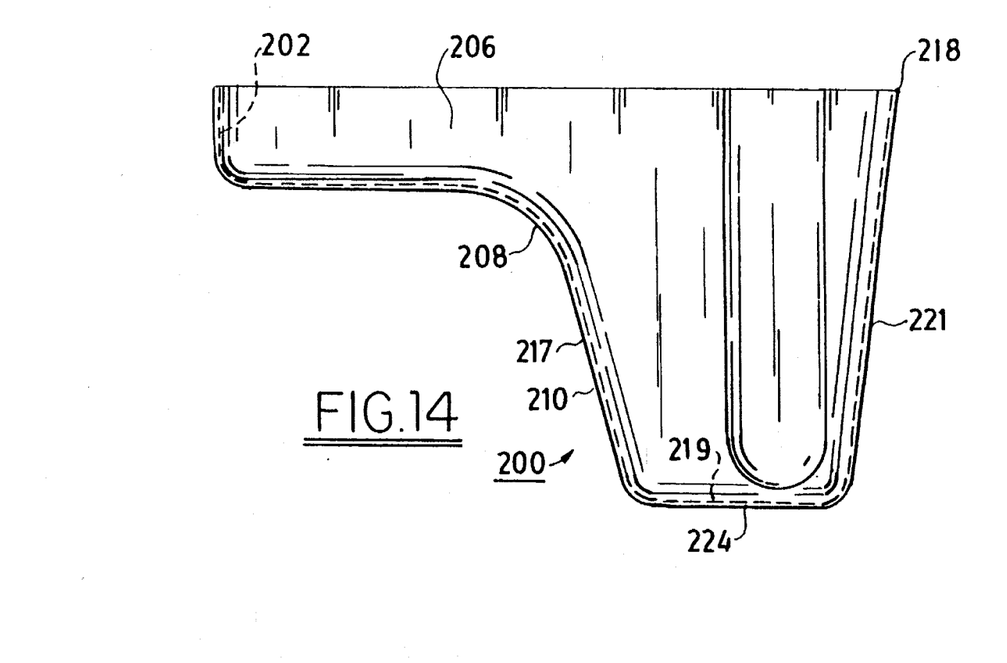
FIG. 14 is a receptacle which may be used in conjunction with the handpiece applicator of FIG. 6 to catch water splashed from the ear of a patient.

In one aspect of applicant's invention, when either handpiece 3 or handpiece 40 is used to direct water into a patient's ear, a receptacle is used to catch water splashed from such ear.

One preferred embodiment of such a receptacle is illustrated in FIG. 14, which presents a side view of the receptacle. Referring to FIG. 14, it will be seen that receptacle 200 is preferably an integral structure, consisting essentially of plastic material, whose preferred interior configuration is illustrated by dotted line 202. Front portion 206 of receptacle 200 is adapted to fit over a patient's shoulder, the curved portion 208 and the inclined portion 210 of the receptacle being adapted to conform to the patient's shoulder and chest, respectively.

Figure 15:
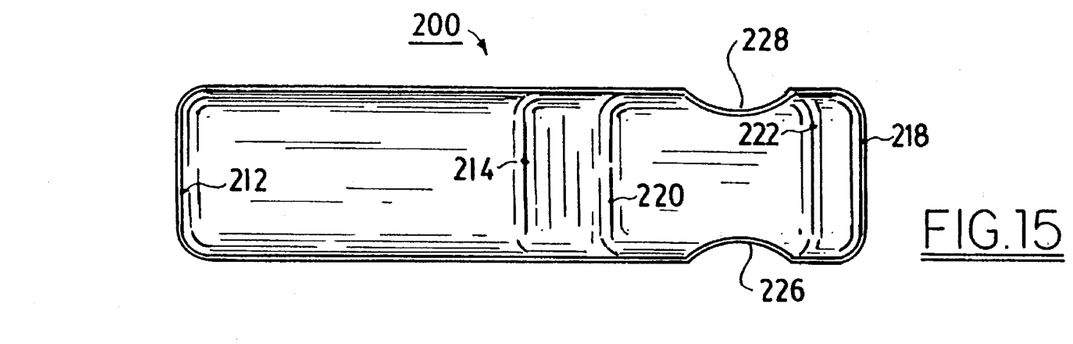
FIG. 15 is a top view of the receptacle of FIG. 14.
Figure 16:
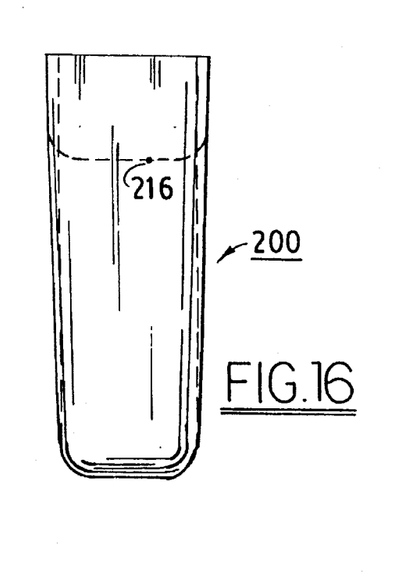
FIG. 16 is a front view of the receptacle of FIG. 14.

FIG. 15 is a top view of receptacle 200. Referring to FIG. 15, it will be seen that a relatively narrow trough is formed between points 212 and 214; the depth of this trough may be seen be referring to FIG. 16, it being approximately equal to the distance between points 214 and 216.

Referring again to FIG. 15, a deeper fluid receptacle is formed between points 214 and 218. The left wall 217 of this receptacle extends downwardly and on an incline from the top of receptacle 200 (at point 214) to the bottom of the receptacle 200 (at point 220). The bottom wall 219 of this receptacle extends substantially horizontally from point 220 to point 222, along the bottom 224 of receptacle 200. The right wall 221 of receptacle 200 extends upwardly from point 222 to point 218.

Referring again to FIG. 15, and in the preferred embodiment illustrated therein, it will be seen that recesses 226 and 228 are formed on the right side and the left side of receptacle 200, respectively.

In one preferred embodiment, controller 42 is so programmed that, when handpiece 40 is disposed in storage receptacle 140, the controller 42 will maintain the temperature of the water coursing through the system at the desired point. If no activity occurs for a specified period of time, such as five minutes, the controller will turn the unit off.

In one embodiment, not shown, a removable plug is provided on the bottom of controller 42 to allow water to be drained from the reservoir in the controller.

Irrigation device with in-line heater

Figure 17:
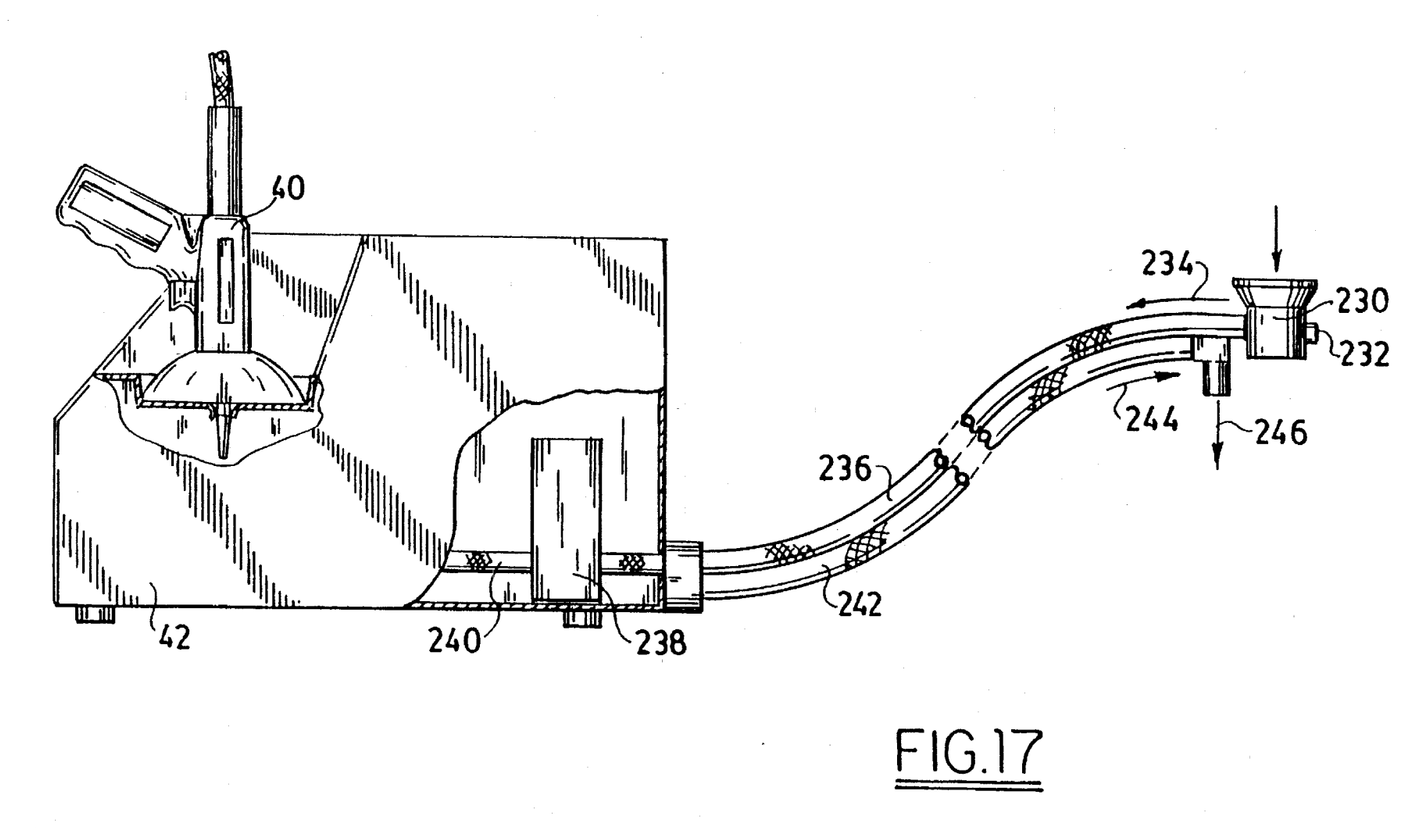
FIG. 17 is a side view, partially broken away, an automated ear cleaning apparatus comprised of an in line heater.

FIG. 17 is a side view of another preferred embodiment of an irrigation device which is comprised of handpiece 40 and controller 42. In this embodiment, water is fed from a source (such as a water tap, not shown) to an adaptor 230 which, in the preferred embodiment illustrated, is comprised of a quick release button 232.

Referring again to FIG. 17, water flows in the direction of arrow 234 through flexible tubing 236 to in-line heater 238 and, thereafter, through conduit 240. Overflow fluid, or fluid at too high a pressure, or fluid which is outside of the desired temperature range, may be passed via overflow tube in the direction of arrows 244 and 246 to a waste outlet (not shown) such as a sink.

The function of in-line heater 238 is to heat the incoming fluid to the desired temperature (preferably a temperature within the range of from about 36 to about 38 degrees Centigrade) substantially instantaneously, when demanded by the system. Thus, for example, in-line heater 238 may be connected to switch means (not shown) which allows one to turn such heater off and on. When heater 238 is in the on mode, fluid passing through it is heated substantially instantaneously to the desired temperature.

One may use many of the commercially available in-line heaters as heater 238 and equip these heaters with thermostat means which will provide the desired temperature regulation. Thus, by way of illustration and not limitation, one may use commercially available tankless water heaters such as, e.g., the model S-23L "Insta-Flow" heater available from Chronomite Laboratories of 21011 South Fiugueroa, Carson Calif. Thus, e.g., one may use the "Corona CTH 25" heater available from Tri-American Products Corporation of 1874 S.W. 16th Terrace, Miami, Fla. 33145. Many other sources of such in-line heaters will be readily apparent to those skilled in the art.

The aforementioned commercially available in-line heaters are equipped with self-contained temperature regulating means usually containing a thermostat and/or a thermistor. As is apparent to those skilled in the art, these means may be adjusted and/or modified to provide temperature regulation within the desired range.

Referring again to FIG. 17, the output from in-line heater 238 is passed via line 240. In one embodiment, not shown, the output is passed to a valve (not shown) and then to pump 158 (not shown in FIG. 17). In another embodiment, not shown, the output is passed directly from the valve 241 to pop off valve 178 (see FIG. 18). In this latter embodiment, the pressure of the fluid supplied is sufficient to cause the fluid to pass to pop off valve 178 without the need for pump 158. Thus, for example, when the apparatus is hooked up to a source of city water, such water is usually at a pressure of from about 30 to about 120 pounds per square inch and, generally, at a pressure of from about 40 to about 60 pounds per square inch.

Figure 18:
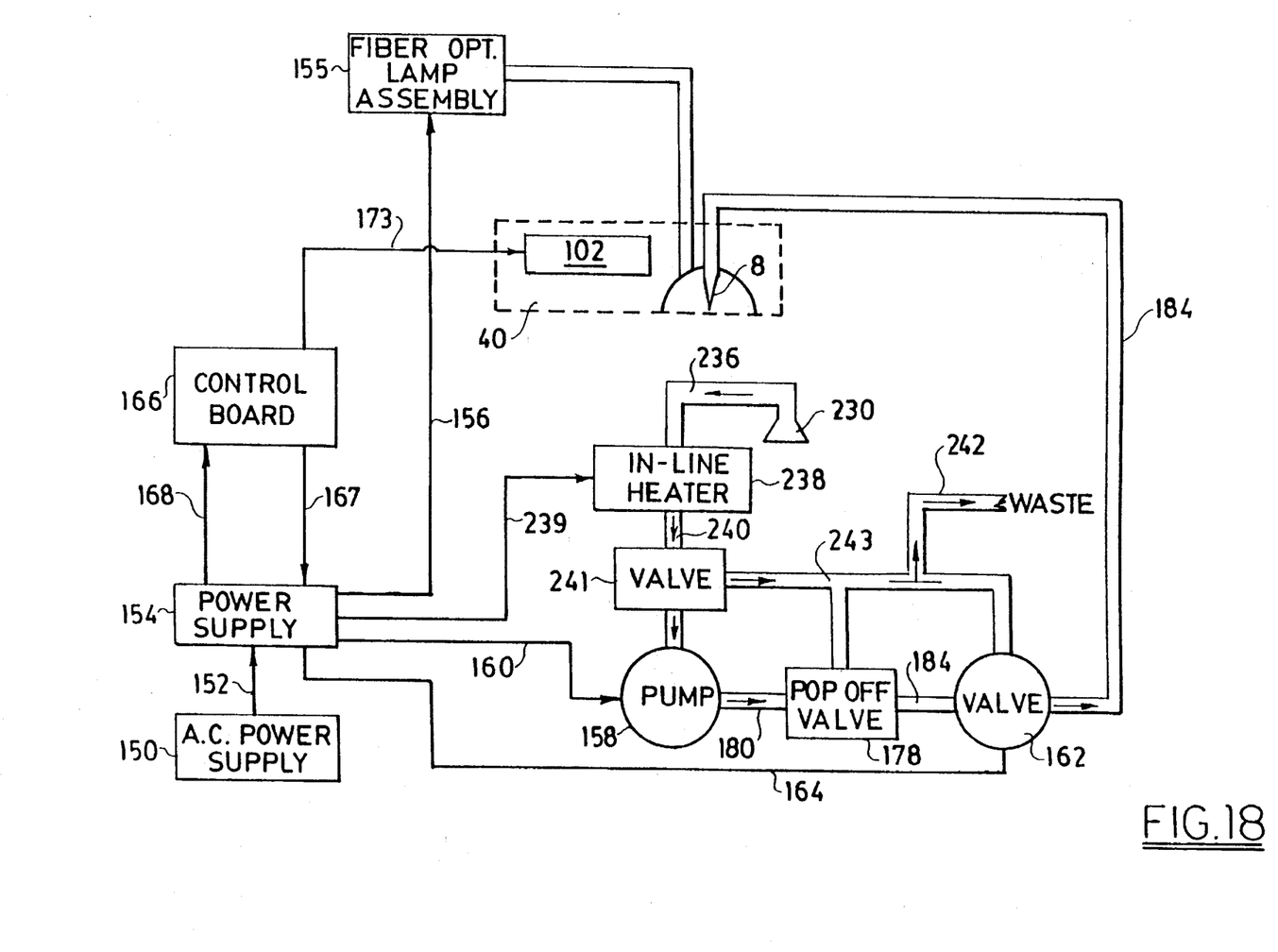
FIG. 18 is a block diagram illustrating the operation of the apparatus of FIG. 17.

FIG. 18 is a block diagram illustrating the structure of the embodiment of FIG. 17.

Referring to FIG. 18, and in one of the preferred embodiments depicted therein, the fluid flowing into tube 236 is heated by in-line heater 238, which may be furnished with power from power supply 154 via line 239. The output from in-line heater 238 is passed via line 240 to valve 241. When fluid is not being dispensed by the apparatus, valve 241 diverts the fluid via lines 243 and 242 to waste. When fluid is being dispensed by the system, valve 241 allows such fluid to flow via either to pop off valve 178 or to pump 158, depending upon what configuration is used in the system.

In the configuration shown in FIG. 18, when the system is dispensing fluid, the fluid flows from valve 241 to pump 158 and thence to pop off valve 178. In another configuration, not shown, the pump 158 is eliminated and, when the system is dispensing fluid, fluid flows directly from valve 241 to pop off valve 178.

Irrigation device with external reservoir

In one preferred embodiment, illustrated in FIG. 9, the irrigation apparatus of this invention is comprised of a reservoir; see, e.g., element 174 in FIG. 9. In this embodiment, the reservoir may either be internal (that is, contained within the device) or external (contained outside of the device).

Figure 19:
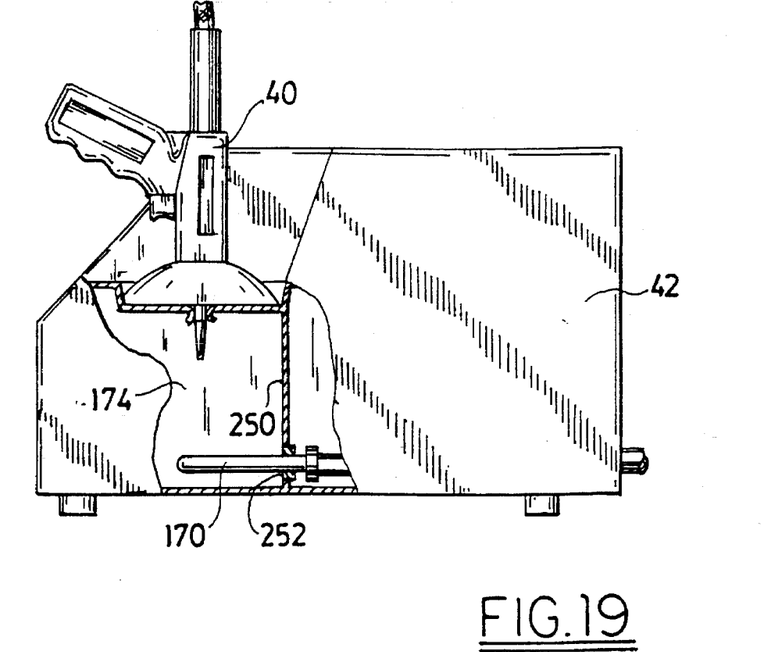
FIG. 19 is a side view of an automated ear cleaning apparatus which is comprised of a controller and an external reservoir.
Figure 20:
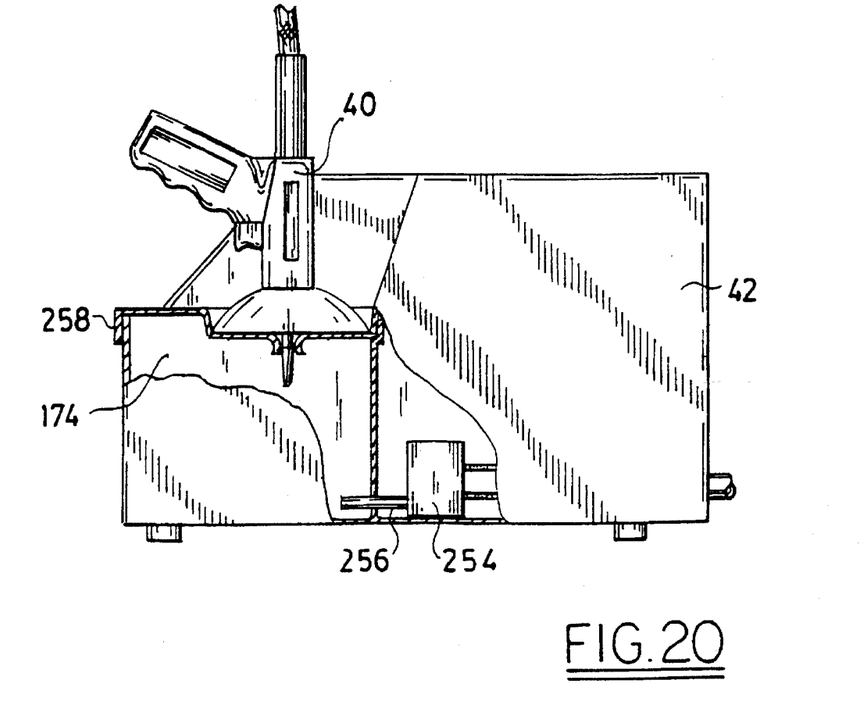
FIG. 20 is a side view of another embodiment of an automated ear cleaning apparatus which is comprised of a controller and an external reservoir.

In one aspect of this embodiment, illustrated in FIGS. 19 and 20, the reservoir 174 is located externally from the housing containing controller 42.

In the embodiment illustrated in FIG. 19, an immersible heater 170 is disposed within reservoir 174; this immersible heater may be controlled in the manner illustrated in FIG. 9. The heater element extends through the wall 250 of reservoir 174 and is preferably sealed by sealing means 252.

By comparison, the apparatus depicted in FIG. 20, which also is comprised of an external reservoir 174, utilizes a heater 254 disposed within controller 42. In the operation of this device, fluid (such as water) is drawn via line 256 from reservoir 174 to heater 254 and, after having been heated to the appropriate temperature, is pumped back to reservoir 174 by means not shown.

In one preferred embodiment, where an external reservoir 174 is utilized, it is preferably constructed of material which is preferably transparent (such as transparent acrylonitrile butadiene styrene [ABS] or transparent acrylic). In this embodiment, one may eliminate the full/refill gauge 130.

As will be apparent to those skilled in the art, the use of an external reservoir 174 facilitates the cleaning of the reservoir. In one embodiment, not shown, the reservoir 174 is removably attached to controller 42. In another embodiment, the reservoir 174 is comprised of a snap off lid 258 (see FIG. 20).

Hand-held irrigation device

Figure 21:
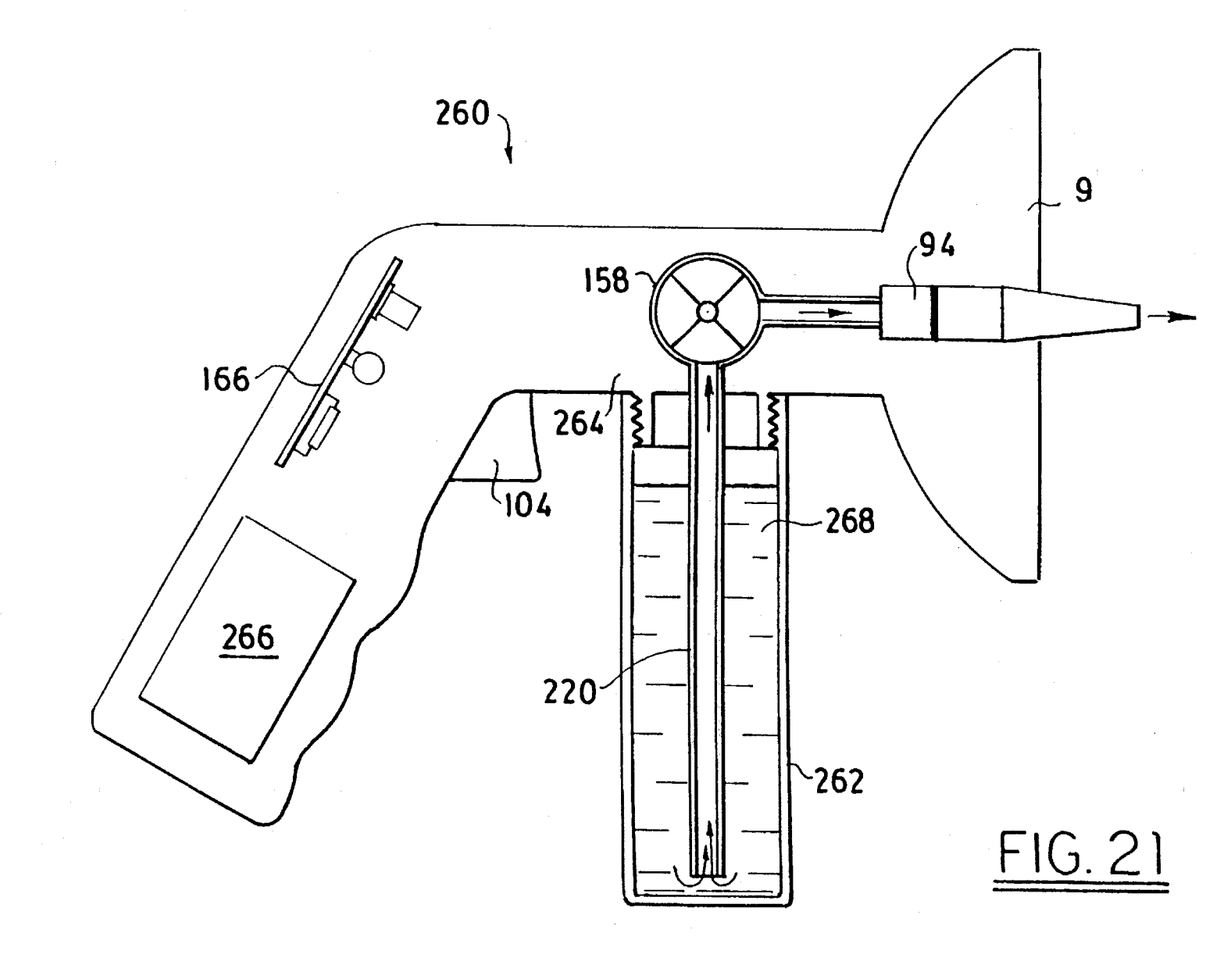
FIG. 21 is a side view of a self-contained, hand-held ear cleaning apparatus.

FIG. 21 is a side view of a preferred, hand-held irrigation device 260 which does not require any external connections. Referring to FIG. 21, irrigation device 260 is comprised of removable reservoir 262, which may be removably attached by conventional means (such as screw threads, not shown, molded into the body of device 260) to body 264. Pump 158 is disposed within body 264 and is electrically connected (by means not shown) to control board 166 which in turn, is electrically connected (by means not shown) to battery pack 266. Pump 266 hydraulically communicates with fluid 268 within reservoir 262 by means of tube 270. The unit may be actuated by means of trigger switch 104, which is electrically connected to control board 166 by means not shown.

In one embodiment, not shown, the fluid 268 in reservoir 262 is heated to the desired temperature prior to the time the filled reservoir 262 is attached to body 264.

In another embodiment, not shown, device 260 is comprised of a temperature sensor which, when the temperature of the fluid within reservoir 262 is lower than the desired temperature, means are provided for preventing the dispensing of the fluid.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A system for cleaning a patient's ear, wherein said system is comprised of a control unit, a portable applicator, means for producing a lighted image of a patient's ear, means for magnifying said lighted image of said patient's ear, means for producing a signal by actuating a control device, means for limiting fluid flow when a fluid pressure exceeds a certain limit, and means for stopping fluid flow when a fluid temperature exceeds a certain limit, wherein:

(a) said control unit is comprised of a heater means and heater control means for maintaining the temperature of fluid within preset limits, a fluid supply line, and flow control means for limiting the pressure and flow rate of said fluid;

(b) said portable applicator is operatively connected to said control unit and is comprised of a handpiece, a flow-directing first orifice connected to said fluid supply line, and a signal generator to generate said control signal to said flow control means; and (c) said means for limiting fluid flow when the fluid pressure exceeds a certain limit is connected to said fluid supply line and is configured to divert a portion of the fluid flow when fluid pressure limits are exceeded.

2. The system as recited in claim 1, wherein said system is comprised of a fluid reservoir.

3. The system as recited in claim 2, wherein said control unit is mounted within a housing.

4. The system as recited in claim 3, wherein said reservoir is disposed outside of housing.

5. The system as recited in claim 4, wherein said reservoir is removably attached to said housing.

6. The system as recited in claim 4, wherein said reservoir is comprised of a removable lid.

7. The system as recited in claim 1, wherein said system is comprised of fluid input line.

8. The system as recited in claim 7, wherein said fluid input line is hydraulically connected to an in-line heater.

9. The system as recited in claim 8, wherein said in-line heater is comprised of a fluid output line.

10. The system as recited in claim 9, wherein said fluid output line of said in-line heater is hydraulically connected to a first valve.

11. The system as recited in claim 10, wherein said first valve has a fluid output line.

12. The system as recited in claim 11, wherein said fluid output line of said first valve is hydraulically connected to a pump.

13. The system as recited in claim 11, wherein said fluid output line of said first valve is hydraulically connected to a second valve.

14. A system for cleaning a patient's ear, wherein said system is comprised of a control unit, a portable applicator, means for producing a signal by actuating a control device, means for limiting fluid flow when a fluid pressure exceeds a certain limit, and means for stopping fluid flow when a fluid temperature exceeds a certain limit, wherein:

(a) said control unit is comprised of a heater means and heater control means for maintaining the temperature of fluid within preset limits, a fluid supply line, and flow control means for limiting the pressure and flow rate of said fluid;

(b) said portable applicator is operatively connected to said control unit and is comprised of a handpiece, a flow-directing first orifice connected to said fluid supply line, and a signal generator to generate said control signal to said flow control means; and (c) said means for limiting fluid flow when the fluid pressure exceeds a certain limit is connected to said fluid supply line and is configured to divert a portion of the fluid flow when fluid pressure limits are exceeded.

15. The system as recited in claim 14, wherein said system is comprised of a reservoir.

* * * * *